(12) United States Patent
Craig et al.

(10) Patent No.: US 6,972,198 B2
(45) Date of Patent: Dec. 6, 2005

(54) METHODS AND COMPOSITIONS USING PROTEIN BINDING PARTNERS

(75) Inventors: Roger K. Craig, Cheshire (GB); John Colyer, West Yorkshire (GB)

(73) Assignee: Cyclacel, Ltd., Dundee Technopole (GB)

( * ) Notice: Subject to any disclaimer, the term of this patent is extended or adjusted under 35 U.S.C. 154(b) by 137 days.

(21) Appl. No.: 09/511,776

(22) Filed: Feb. 24, 2000

(65) Prior Publication Data

US 2003/0082827 A1 May 1, 2003

Related U.S. Application Data

(63) Continuation-in-part of application No. 09/258,452, filed on Feb. 26, 1999, now abandoned.

(51) Int. Cl.[7] .......................... G01N 37/00; G01N 21/00
(52) U.S. Cl. ............................ 436/164; 435/4; 435/6; 435/7.1; 435/7.9; 435/7.92; 435/968; 436/501; 436/528; 436/538; 436/546; 436/547; 436/164; 436/172; 436/56; 436/519
(58) Field of Search ........................ 435/4, 6, 7.1, 7.6, 435/7.71, 7.92–7.95, 7.9, 18, 21, 183, 960, 961, 968; 436/501, 518, 538, 542, 546, 547, 164, 172, 528, 819; 536/23.4, 23.5; 422/56, 57, 61

(56) References Cited

U.S. PATENT DOCUMENTS

| | | | | |
|---|---|---|---|---|
| 4,444,879 A | * | 4/1984 | Foster et al. | 435/7.1 |
| 5,891,641 A | * | 4/1999 | Prusiner et al. | 435/7.1 |
| 5,998,204 A | * | 12/1999 | Tsien et al. | 435/325 |
| 6,203,994 B1 | * | 3/2001 | Epps et al. | 435/7.1 |

FOREIGN PATENT DOCUMENTS

| | | | | |
|---|---|---|---|---|
| EP | 0244221 | | 11/1987 | ........... C07K/15/00 |
| EP | 0613007 | | 8/1994 | ........... G01N/33/68 |
| EP | 0613007 A2 | * | 8/1994 | ................ 435/7.92 |
| EP | 0770876 A1 | * | 2/1997 | |
| GB | 2111201 | | 6/1983 | ........... G01N/33/54 |
| GB | 2300859 | | 11/1996 | ........... A61K/47/48 |
| WO | WO-96/05847 A1 | * | 2/1996 | ................. 435/7.6 |
| WO | WO96/15153 | | 5/1996 | ........... C07K/16/28 |
| WO | WO 96/33414 | | 10/1996 | ......... G01N/33/569 |
| WO | WO 97/20952 | | 6/1997 | ............. C12Q/1/68 |
| WO | WO 98/09169 | | 3/1998 | ......... G01N/33/573 |
| WO | WO-98/37411 A1 | * | 8/1998 | ................. 435/7.1 |
| WO | WO 98/40477 | | 9/1998 | ........... C12N/15/00 |
| WO | WO-98/41872 A1 | * | 9/1998 | ................. 435/7.1 |

OTHER PUBLICATIONS

Kinjo et al., Ultrasensitive hybridization analysis using Fluorescence Correlation Spectroscopy, Nucleic Acids Research 23(10):1795–1799 (1995).*

(Continued)

*Primary Examiner*—Chris Chin
*Assistant Examiner*—Gailene R. Gabel
(74) *Attorney, Agent, or Firm*—Kathleen M. Williams; Mark J. FitzGerald; Palmer & Dodge, LLP

(57) ABSTRACT

The invention relates to a method for determining the conformational state of a protein, comprising the steps of: a) providing a first binding partner which is capable of binding to the protein in a manner dependent on the conformational state of the protein and which generates a signal in a manner dependent on the binding of the first binding partner to the protein; and b) contacting the protein with the first binding partner and determining the conformational state of the protein by assessing the labelling of the protein by the binding of the first binding partner.

12 Claims, 4 Drawing Sheets

OTHER PUBLICATIONS

Ha et al., Single molecule fluorescence spectroscopy of enzyme conformational dynamics and cleavage mechanism, Proc. Natl. Sci. USA 96(3): 893–898 (1999).*

Lillo et al.., Design and characterization of a multi–site fluorescence energy–transfer system for protein folding studies: A steady state and time–resolved study of the yeast phosphoglycerate kinase, Biochemistry 36(37): 11261–11272 (1997).*

Wolf, et al. (1998). "Interactions of calmodulin with metal ions and with its target proteins revealed by conformation–sensitive monoclonal antibodies," *Journal of Molecular Recognition* 11:14–19.

Ivnitksi, et al. (1998). "Anamperometric biosensor for real–time analysis of molecular recognition," *Bioelectrochemistry and Bioenergetics* 45:27–32.

D'Ettore, et al. (1997). "Functional epitope mapping of human interleukin–1beta by surface plasmon resonance," *Eur. Cytokine Netw.* 8(2): 161–171.

Heffetz, et al. (1991). "Generationa nd Use of Antibodies to Phosphothreonine," Methods in Enzymology 201:44–53.

International Search Report of Application No. GB 9904395.2

International Search Report of Application No. PCT/GB00/00668.

Copy of Form PTO–1449 filed Feb. 24, 2000, in U.S. Appl. No. 09/511,776.

Kinjo and Rigler, *NAR* 23:1795–1799 (1995).

* cited by examiner p47^phox-coiled coil fusion        Fluorescein labelled p47^phox Peptide 3

No binding

Incubate with PKC

N

Specific binding

METHODS AND COMPOSITIONS USING PROTEIN BINDING PARTNERS

This application is a continuation-in-part of U.S. Ser. No. 09/258,452, filed Feb. 26, 1999 now abandoned.

FIELD OF THE INVENTION

The present invention relates to an assay for the determination of the conformations of a polypeptide or protein. In particular, the invention relates to an assay which employs at least one labelled binding partner capable of binding to the protein in a manner dependent on the conformational state of the protein.

BACKGROUND

Proteins may exist in more than one possible conformations, some of which may possess activities which differ from those of alternative conformations of the same protein. For example protein kinase enzymes frequently are held in an inactive form by the occupancy of the active site by a distant domain of the same polypeptide. This is known as pseudo-substrate inhibition. To become active this section of the protein must be removed from the active site, which can either be achieved by post transitional modification of the polypeptide, or some other stimulus for conformation change such as ligand binding (for example by cyclic GMP). In such cases the active and inactive form of the protein can be identified through the conformational dissimilarity of the two states.

In other instances diseases can arise from a change in conformation of protein. Prion proteins are membrane-associated cellular proteins that can change to an abnormal conformational form which then deposit in areas of the brain. This underlies Bovine Spongiform Encephalopathy (BSE), the sheep disease Scrapie, and the human disease Creutzfeldt-Jakob Disease (CJD). The switch between normal cellular prion protein forms and the abnormal version of the prion protein is a post-translational event, although the molecular basis for this has not been fully described.

Alzheimer's Disease has a similar pathology albeit involving a different protein. The amyloid precursor protein, again a normal cellular membrane protein, can be processed by proteolysis in a way which is harmless or in a way which generates a fragment that deposits in the brain bringing about the symptoms of Alzheimer's Disease.

A further conformational variation in proteins can arise from the expression of different forms of the same protein. These sequence variants of a protein are known as isoforms of the protein. Isoforms of a protein catalyse the same chemical reaction but may exhibit distinct kinetic, regulatory or other properties. Isoforms can arise from the alternative amino acid sequence of a single polypeptide or they can arise from the differential combination of two or more polypeptides from a pool of sub-units of different amino acid sequence. An example of the former is the protein kinase C enzyme family, and the latter includes protein kinase A and calmodulin dependent kinase II. Enzyme isoforms are usually tissue specific in that the environment found in one tissue suits the kinetic properties of the isoform found there, whereas the environment of a separate tissue is less appropriate for that isoform, but is satisfied by a different enzyme isoform expressed in that second tissue.

In clinical situations that involve cell or tissue damage, the serum of a patient contains enzymes, which are normally intracellular or otherwise tissue specific, but have been released from the damaged tissue. Routine pathology investigations monitor the isoform specificity of serum enzymes and deduce a site of tissue damage from the isoform profile. This is typically done using convoluted assays that examine the enzymatic properties of those serum enzymes in combination with antibodies that might inhibit one isoform of the enzyme.

SUMMARY OF THE INVENTION

The present invention provides a method by which conformational change in proteins may be monitored in real time, or otherwise detected. According to a first aspect, therefore, the present invention provides a method for determining the conformational state of a protein, comprising the steps of:

a) providing a first binding partner which is capable of binding to the protein in a manner dependent on the conformational state of the protein and which is capable of generating a signal in a manner dependent on the binding of the first binding partner to the protein; and b) contacting the protein with the first binding partner and determining the conformational state of the protein by assessing the labelling of the protein by the binding of the first binding partner.

As used herein, the term "protein" refers to a polymer in which the monomers are amino acids and are joined together through peptide or disulphide bonds. "Protein" refers to a full-length naturally-occurring amino acid chain or a fragment thereof, such as a selected region of the polypeptide that is of interest in a binding interaction, or a synthetic amino acid chain, or a combination thereof. "Fragment thereof" thus refers to an amino acid sequence that is a portion of a full-length protein, between about 8 and about 500 amino acids in length, preferably about 8 to about 300, more preferably about 8 to about 200 amino acids, and even more preferably about 10 to about 50 or 100 amino acids in length. Additionally, amino acids other than naturally-occurring amino acids, for example β-alanine, phenyl glycine and homoarginine, may be included. Commonly-encountered amino acids which are not gene-encoded may also be used in the present invention. All of the amino acids used in the present invention may be either the D- or L-optical isomer. The D-isomers are preferred for use in a specific context, further described below. In addition, other peptidomimetics are also useful, e.g. in linker sequences of polypeptides of the present invention (see Spatola, 1983, in *Chemistry and Biochemistry of Amino Acids, Peptides and Proteins*, Weinstein, ed., Marcel Dekker, New York, p. 267). In general, the term "protein" is not intended to convey any significant difference over the term "polypeptide". A protein, however, explicitly includes structures which comprise two or several polypeptide chains held together by covalent or non-covalent bonds.

In general, proteins according to the invention are naturally-occuring, full length proteins which it is desired to assay by the method of the invention. "Naturally-occurring" as used herein, as applied to a protein, refers to the fact that the protein can be found in nature. One such example is a protein that is present in an organism (including a virus) that can be isolated from a source in nature. The invention, however, is also applicable to the determination of the conformational state of engineered proteins, which are not found in nature, but which may be capable of having a biological effect.

As used herein, the term "binding partner" refers to a polypeptide or other agent that binds to (associates with) a protein according to the invention. Exemplary binding partners are described below; however, the term generally includes ligands such as antibodies and other polypeptides capable of binding to proteins, chemical ligands, nucleic acid ligands such as RNA aptamers and natural ligands such as those normally associated with the protein.

As used herein, the term "associates" or "binds" refers to binding partners as described herein having a binding constant sufficiently strong to allow detection of binding to the protein by a detection means. Preferably, the binding partners, when associated or bound, are in physical contact with each other and have a dissociation constant (Kd) of about 10 $\mu$M or lower. The contact region may include all or parts of the two molecules. Therefore, the terms "substantially dissociated" and "dissociated" or "substantially unbound" or "unbound" refer to the absence or loss of contact between such regions, such that the binding constant is reduced by an amount which produces a discernible change in a signal compared to the bound state, including a total absence or loss of contact, such that the proteins are completely separated, as well as a partial absence or loss of contact, so that the body of the proteins are no longer in close proximity to each other but may still be tethered together or otherwise loosely attached, and thus have a dissociation constant greater than 10 $\mu$M (Kd). In many cases, the Kd will be in the mM range. The terms "complex" and, particularly, "dimer", "trimer", "tetramer", "multimer" and "oligomer", as used herein, refer to the polypeptides, peptides, proteins, domains or subunits in the associated or bound state. More than one molecule of each of the two or more polypeptides may be present in a complex, dimer, multimer or oligomer according to the methods of the invention.

The "conformational state" of a protein, as referred to herein, includes any one or more of its primary, secondary, tertiary and quaternary structure. The method of the invention is applicable to the determination of any structural feature of a protein which is manifested as a three-dimensional structural property. Thus, whilst the invention is not directed to determination of primary structure per se, changes in primary structure will usually manifest themselves as alterations in higher order structure; the invention therefore allows changes in primary structure to be determined via their effects on the tree-dimensional structure of the protein. Proteins with different conformational states include, but are not limited to, multimers which have lost or gained one or more monomers; proteins which have been modified post-translationally, such as by acylation, glycosylation, ubiquitination, phosphorylation, proteolysis or in any other way; proteins which have bound to a natural or unnatural ligand; in particular, proteins which have bound to a ligand which ligand causes a conformational change at a site remote from ligand binding when binding takes place; and proteins which in change structure for reasons which are at present unknown, such as prions.

Accordingly, in a preferred aspect, the invention provides a method for measuring enzyme activity wherein the conformation of a protein is dependent upon the post-translational modification activity of an enzyme, the method comprising the steps of:

a) contacting a protein comprising a site for post-translational modification with the enzyme;

b) providing a first binding partner which is capable of binding to the protein in a manner dependent on the post-translational modification of the protein by the enzyme and which generates a signal in a manner dependent on said post-translational modification; and c) contacting the protein with the first binding partner and determining the post-translational modifying activity of the enzyme.

The present invention permits the determination of the conformational state of a polypeptide by providing a multi-layer detection protocol. A first feature thereof is that the binding of the first binding partner to the protein is dependent on the conformational state of the protein. A second feature is that the binding of the binding partner to the protein is in itself a detectable event.

Conformation-dependent binding is a feature of many possible binding partners which may be used in the context of the present invention. For example, binding partners such as antibodies, which bind to highly determinate three-dimensional epitopes, or ligands which bind to conformationally complementary sites in proteins, are capable of conformation-dependent binding. Such binding partners may be natural ligands for the protein, such as natural activators or inhibitors, or artificial compounds known or suspected to bind to the protein. Alternatively, ligands may be designed, by structural analysis of the protein or of known protein ligands and the design of novel binding partners or mimics of known binding partners based on this knowledge. For instance, the X-ray crystallographic structure of a protein in a given conformational state may be used to design molecules capable of binding to the protein in that conformational state. Comparison may be made with X-ray crystallographic structures of the protein in an alternative conformational state in order to select a binding partner which will be expected to bind in a conformationally-dependent manner.

Antibodies, especially scFv and other antibodies which may be selected by any applicable selection technique, including for example phage display, are also useful as binding partners. Antibodies may be specifically selected for their ability to bind selectively to a chosen conformation of the protein by established techniques, as described further below.

Detecting the binding of the binding partner to the protein may be effected in a number of ways. In a first configuration of the invention, the protein may be bound to a solid phase substrate, such as a bead or a matrix, from which unbound binding partner may be removed. The unbound binding partner may for example be washed away, or the solid phase may itself be removed from the binding partner. Detection of the binding partner may then be performed, and only the binding partner which has remained bound to the protein is detected.

In a second configuration, the association of the protein and the binding partner may be measured by mass, such as by surface plasmon resonance. In this example, binding of the binding partner to the protein causes a change in the mass thereof; unbound binding partner causes no change in mass, and is therefore not detectable. In a third configuration, the binding partner may be labelled with a fluorescent label and binding detected by FCS. FCS, as further described below, is dependent on the size of a fluorescent molecule as being determinative of its rate of movement within a measurement cell. A binding partner which is bound to a protein will demonstrate a reduced rate of movement, compared to unbound binding partner, as a result of its increased size. An alternative to FCS is fluorescence anisotropy. Fluorescence anisotropy relies on the measurement of the rotation of fluorescent groups. Larger multimers of polypeptides rotate more slowly than monomers, allowing the formation of multimers to be monitored.

In a fourth configuration, both the first and second binding partners may be labelled, and the labels detected by FRET. As described below, FRET occurs between two fluorescent labels which fluoresce in close proximity with each other. Thus, the binding of the binding partner(s) to the protein will be detectable as a result of FRET. Similar configurations would include the use of enzyme domains, which combine to form a reporter enzyme; the use of constituent domains of a transcription factor, such as in a two-hybrid assay; the use of a fluorescent label and a quencher molecule, capable of quenching emissions from the label; and other configurations which will be apparent to those skilled in the art.

A number of the foregoing configurations require a second binding partner. This may be required to deliver a second label, or to immobilise the polypeptide to a solid phase, or as a capture ligand to permit isolation of the polypeptide. Preferably, the second binding partner does not bind in a strictly conformation-dependent manner, but is capable of binding to a subset of possible conformations, or even substantially all conformations, of the protein.

In a further aspect, the present invention relates to a first binding partner which is capable of binding to a protein, which binding partner:

a) binds to the protein in a manner dependent on the conformational state of the protein; and b) is detectable in a manner dependent on its binding to the protein.

As set forth above, a binding partner according to the invention is preferably an antibody, such as a single-chain antibody or scFv selectable by phage display, or a polypeptide ligand.

Binding partners according to the invention may be packaged in the form of kits, together with necessary packaging material, for sale in, for example, diagnostic applications. Kits according to the invention may additionally comprise a second binding partner. Either or both of the first and second binding partners may be labelled.

Kits may moreover comprise the protein whose conformation it is desired to study, buffers or other standard reagents necessary for the performance of an assay according to the invention, and/or signal detection means designed to allow detection of the bound first binding partner in the assay. In an advantageous embodiment, kits according to the invention may be provided for the detection of a ligand for a protein in a sample, where the ligand binds to the protein and induces a conformational change therein. In such a kit, the protein and first binding partner are provided, optionally together with a second binding partner. The protein is advantageously immobilised onto a solid substrate, to which the sample may be applied for analysis.

DETAILED DESCRIPTION OF THE INVENTION

Figure 1:
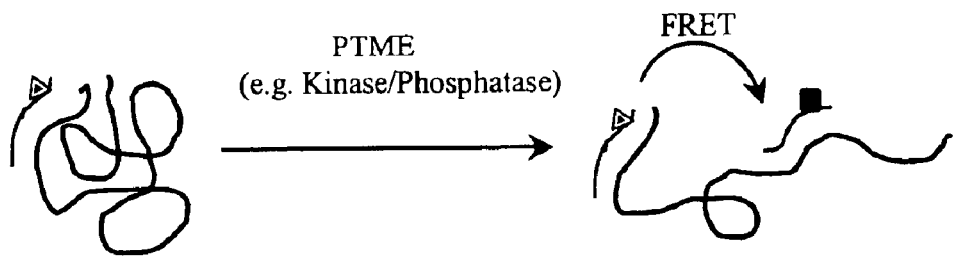
FIG. 1. Measurement of PTME activity as a function of conformational change.

Generally, the nomenclature used herein and the laboratory procedures in cell culture, molecular genetics, and nucleic acid chemistry and hybridisation described below are those well known and commonly employed in the art. Standard techniques are used for recombinant nucleic acid methods, polynucleotide synthesis, and microbial culture and transformation (e.g., electroporation, lipofection). Generally, enzymatic reactions and purification steps are performed according to the manufacturer's specifications. The techniques and procedures are generally performed according to conventional methods in the art and various general references (see generally, Sambrook et al., *Molecular Cloning: A Laboratory Manual*, 2d ed. (1989) Cold Spring Harbor Laboratory Press, Cold Spring Harbor, N.Y., which is incorporated herein by reference) which are provided throughout this document. The nomenclature used herein and the laboratory procedures in analytical chemistry, organic synthetic chemistry, and pharmaceutical formulation described herein are those well known and commonly employed in the art. Standard techniques are used for chemical syntheses, chemical analyses, pharmaceutical formulation and delivery, and treatment of patients.

The present invention may be configured in a number of ways. Exemplary embodiments of the invention are set forth below.

Protein Conformation

Proteins may be induced to change conformation, or oscillate between two or more conformational possibilities, as a result of a number of phenomena. The invention accordingly provides a means by which such phenomena may be assessed.

An example of such a phenomenon is ligand binding. Many proteins are induced to conformational change upon the binding of the ligand, which is not limited to change at or near the ligand binding site. Often, the conformational change in the protein is closely linked to its biological activity. An example of conformational change induced by ligand binding is calcium binding by the protein calmodulin. This brings about a large change in the conformation of calmodulin. A further example is inositol trisphosphate binding to the IP3 receptor; a still further example is cyclic GMP binding to the protein kinase G enzyme. Each of these binding events triggers a conformational change in the protein which is detectable by the method of the present invention.

Conformational change may moreover be induced by post-translational modification of a protein. This could take the form of residue modification, such as tyrosine, serine, threonine, histidine or aspartic acid phosphorylation. Phosphorylation of ion channel proteins, for instance the L type calcium channel, the sodium channel and the GABA/Kainate receptor are known to alter channel function and are believed to achieve this by changes in conformation of these channels respectively. A second category of example is the insulin receptor signalling protein IRS1 that is heavily phosphorylated in response to insulin binding to the plasma membrane receptor. Upon phosphorylation of IRS1 its conformation changes. Other proteins are modified by different post-translational modification events such as ADP ribose attachment, ubiquitin attachment or sugar attachment. The proto-oncogene C-myc, for example, is glycosylated on threonine 58 in a number of cancers.

A further class of event which leads to conformational change is proteolysis. As well as the obvious truncation of a protein, proteolytic cleavage alters the three-dimensional conformation of a protein in many instances. For example, amyloid precursor proteins are proteolysed by secretin enzymes (α, β, γ), and the conformation of the protein differs as a function of the product sequence generated. Moreover, processing by secretases can generate a form of the APP which deposits in the brain leading to Alzheimer's disease.

A number of proteins are moreover known to change conformation in response to stimuli which remain unknown. For example, prion proteins in diseased states change their conformation from normal to abnormal. This event is post-translational but the stimulus for this transition has not been identified.

Each of the foregoing classes of conformational variation may be assessed by the method of the present invention.

The invention is moreover applicable to the detection of enzyme isoforms in a complex mixture. In this embodiment, a binding second binding partner may bind to a feature common to all isoforms of the enzyme whereas the first binding partner binds to a feature peculiar to a particular isoform. Again the isoform identification can be achieved by examination of the binding of the first and second binding partners to the enzyme. Where the isoform is made up of several polypeptides, the assay may be configured such that the first and second binding partners bind to different polypeptides within the holoenzyme, again in an isoform-specific manner.

Design and Preparation of Binding Partners

As described above, preferred binding partners for use in the present invention include antibodies and peptide ligands, which are advantageously selected by techniques such as phage display. Display and selection of randomised antibody molecules or peptides permits the selection of binding partners capable of binding to any given epitope of a desired protein.

Any selection display system may be used in conjunction with the invention. Selection protocols for isolating desired members of large libraries are known in the art, as typified by phage display techniques. Such systems, in which diverse peptide sequences are displayed on the surface of filamentous bacteriophage (Scott and Smith (1990) *Science*, 249: 386), have proven useful for creating libraries of antibody fragments (and the nucleotide sequences that encoding them) for the in vitro selection and amplification of specific antibody fragments that bind a target antigen. The nucleotide sequences encoding the $V_H$ and $V_L$ regions are linked to gene fragments which encode leader signals that direct them to the periplasmic space of *E. coli* and as a result the resultant antibody fragments are displayed on the surface of the bacteriophage, typically as fusions to bacteriophage coat proteins (e.g., pIII or pVIII). Alternatively, antibody fragments are displayed externally on lambda phage capsids (phagebodies). An advantage of phage-based display systems is that, because they are biological systems, selected library members can be amplified simply by growing the phage containing the selected library member in bacterial cells. Furthermore, since the nucleotide sequence that encode the polypeptide library member is contained on a phage or phagemid vector, sequencing, expression and subsequent genetic manipulation is relatively straightforward.

Methods for the construction of bacteriophage antibody display libraries and lambda phage expression libraries are well known in the art (McCafferty et al. (1990) *Nature*, 348: 552; Kang et al. (1991) *Proc. Natl. Acad. Sci. U.S.A.*, 88: 4363; Clackson et al. (1991) *Nature*, 352: 624; Lowman et al. (1991) *Biochemistry*, 30:10832; Burton et al. (1991) *Proc. Natl. Acad. Sci U.S.A.*, 88: 10134; Hoogenboom et al. (1991) *Nucleic Acids Res.*, 19: 4133; Chang et al. (1991) *J. Immunol.*, 147: 3610; Breitling et al. (1991) *Gene*, 104: 147; Marks et al. (1991) supra; Barbas et al. (1992) supra; Hawkins and Winter (1992) *J. Immunol.*, 22: 867; Marks et al., 1992, *J. Biol. Chem.*, 267: 16007; Lerner et al. (1992) *Science*, 258: 1313, incorporated herein by reference).

One particularly advantageous approach has been the use of scFv phage-libraries (Huston et al., 1988, Proc. Natl. Acad. Sci U.S.A., 85: 5879–5883; Chaudhary et al. (1990) Proc. Natl. Acad. Sci U.S.A., 87: 1066–1070; McCafferty et al. (1990) supra; Clackson et al. (1991) supra; Marks et al. (1991) supra; Chiswell et al. (1992) Trends Biotech., 10: 80; Marks et al. (1992) supra). Various embodiments of scFv libraries displayed on bacteriophage coat proteins have been described. Refinements of phage display approaches are also known, for example as described in WO96/06213 and WO92/01047 (Medical Research Council et al.) and WO97/08320 (Morphosys, supra), which are incorporated herein by reference.

Other systems for generating libraries of polypeptides or nucleotides involve the use of cell-free enzymatic machinery for the in vitro synthesis of the library members. In one method, RNA molecules are selected by alternate rounds of selection against a target ligand and PCR amplification (Tuerk and Gold (1990) *Science*, 249: 505; Ellington and Szostak (1990) *Nature*, 346: 818). A similar technique may be used to identify DNA sequences which bind a predetermined human transcription factor (Thiesen and Bach (1990) *Nucleic Acids Res.*, 18: 3203; Beaudry and Joyce (1992) *Science*, 257: 635; WO92/05258 and WO92/14843). In a similar way, in vitro translation can be used to synthesise polypeptides as a method for generating large libraries. These methods which generally comprise stabilised polysome complexes, are described further in WO88/08453, WO90/05785, WO90/07003, WO91/02076, WO91/05058, and WO92/02536. Alternative display systems which are not phage-based, such as those disclosed in WO95/22625 and WO95/11922 (Affymax) use the polysomes to display polypeptides for selection. These and all the foregoing documents also are incorporated herein by reference.

Using a selection display system as described above, antibodies may be selected which bind specifically to any desired conformational state of a protein. Moreover, peptide ligands may be selected by phage display of peptide libraries, again which are capable of binding to any desired protein epitope.

In an alternative embodiment, binding partners may be designed as peptide ligands, based on natural ligands which are known or suspected to bind to the protein, or based on a structural analysis of the protein and/or ligands thereof.

In a preferred aspect, the crystal structure of a protein or a protein: ligand complex may be used to derive information useful for the design of peptide ligands for the protein. Crystallisation of a protein involves the preparation of a crystallisation buffer, for example by mixing a solution of the protein or protein:ligand complex with a "reservoir buffer", preferably in a 1:1 ratio, with a lower concentration of the precipitating agent necessary for crystal formation. For crystal formation, the concentration of the precipitating agent is increased, for example by addition of precipitating agent, for example by titration, or by allowing the concentration of precipitating agent to balance by diffusion between the crystallisation buffer and a reservoir buffer. Under suitable conditions such diffusion of precipitating agent occurs along the gradient of precipitating agent, for example from the reservoir buffer having a higher concentration of precipitating agent into the crystallisation buffer having a lower concentration of precipitating agent. Diffusion may be achieved for example by vapour diffusion techniques allowing diffusion in the common gas phase. Known techniques are, for example, vapour diffusion methods, such as the "hanging drop" or the "sitting drop" method. In the vapour diffusion method a drop of crystallisation buffer containing the protein is hanging above or sitting beside a much larger pool of reservoir buffer. Alternatively, the balancing of the precipitating agent can be achieved through a semipermeable membrane that separates the crystallisation buffer from the reservoir buffer and prevents dilution of the protein into the reservoir buffer.

In the crystallisation buffer the peptide or peptide/binding partner complex preferably has a concentration of up to 30 mg/ml, preferably from about 2 mg/ml to about 4 mg/ml.

Formation of crystals can be achieved under various conditions which are essentially determined by the following parameters: pH, presence of salts and additives, precipitating agent, protein concentration and temperature. The pH may range from about 4.0 to 9.0. The concentration and type of buffer is rather unimportant, and therefore variable, e.g. in dependence with the desired pH. Suitable buffer systems include phosphate, acetate, citrate, Tris, MES and HEPES buffers. Useful salts and additives include e.g. chlorides, sulphates and further salts known in the art. The buffer contains a precipitating agent selected from the group consisting of a water miscible organic solvent, preferably polyethylene glycol having a molecular weight of between 100 and 20000, preferentially between 4000 and 10000, or a suitable salt, such as a sulphates, particularly ammonium sulphate, a chloride, a citrate or a tartrate.

A crystal of a peptide or peptide/binding partner complex according to the invention may be chemically modified, e.g. by heavy atom derivatisation. Briefly, such derivatisation is achievable by soaking a crystal in a solution containing heavy metal atom salts, or a organometallic compounds, e.g. lead chloride, gold thiomalate, thimerosal or uranyl acetate, which is capable of diffusing through the crystal and binding to the surface of the protein. The location(s) of the bound heavy metal atom(s) can be determined by X-ray diffraction analysis of the soaked crystal, which information may be used e.g. to construct a three-dimensional model of the peptide.

A three-dimensional model is obtainable, for example, from a heavy atom derivative of a crystal and/or from all or part of the structural data provided by the crystallisation. Preferably building of such model involves homology modelling and/or molecular replacement.

The preliminary homology model can be created by a combination of sequence alignment with any similar protein the sequence of which is known, secondary structure prediction and screening of structural libraries.

Computational software may also be used to predict the secondary structure of the peptide ligand or peptide:protein complex. Structural incoherences, e.g. structural fragments around insertions/deletions can be modelled by screening a structural library for peptides of the desired length and with a suitable conformation. For prediction of the side chain conformation, a side chain rotamer library may be employed.

The final homology model is used to solve the crystal structure of the protein by molecular replacement using suitable computer software. The homology model is positioned according to the results of molecular replacement, and subjected to further refinement comprising molecular dynamics calculations and modelling of the inhibitor used for crystallisation into the electron density.

Labelling of Binding Partners

One or more binding partners may comprise a label. Suitable fluorescent labels include fluorophores and fluorescent proteins. As used herein, the terms "fluorophore" and "fluorochrome" refer interchangeably to a molecule which is capable of absorbing energy at a wavelength range and releasing energy at a wavelength range other than the absorbance range. The term "excitation wavelength" refers to the range of wavelengths at which a fluorophore absorbs energy. The term "emission wavelength" refers to the range of wavelength that the fluorophore releases energy or fluoresces.

A non-limiting list of chemical fluorophores of use in the invention, along with their excitation and emission wavelengths, is presented in Table 1.

TABLE 1

| Fluorophore | Excitation (nm) | Emission (nm) | Color |
| --- | --- | --- | --- |
| PKH2 | 490 | 504 | green |
| PKH67 | 490 | 502 | green |
| Fluorescein (FITC) | 495 | 525 | green |
| Hoechst 33258 | 360 | 470 | blue |
| R-Phycoerythrin (PE) | 488 | 578 | orange-red |
| Rhodamine (TRITC) | 552 | 570 | red |
| Quantum Red | 488 | 670 | red |
| PKH26 | 551 | 567 | red |
| Texas Red | 596 | 620 | red |
| Cy3 | 552 | 570 | red |

Examples of fluorescent proteins which vary among themselves in excitation and emission maxima are listed in Table 1 of WO 97/28261 (incorporated herein by reference). These (each followed by [excitation max./emission max.] wavelengths expressed in nanometers) include wild-type Green Fluorescent Protein [395(475)/508] and the cloned mutant of Green Fluorescent Protein variants P4 [383/447], P4-3 [381/445], W7 [433(453)/475(501)], W2 [432(453)/480], S65T [489/511], P4-1 [504(396)/480], S65A [471/504], S65C [479/507], S65L [484/510], Y66F [360/442], Y66W [458/480], I0c [513/527], W1B [432(453)/476(503)], Emerald [487/508] and Sapphire [395/511]. This list is not exhaustive of fluorescent proteins known in the art; additional examples are found in the Genbank and SwissProt public databases.

A number of parameters of fluorescence output are envisaged including:

1) measuring fluorescence emitted at the emission wavelength of the acceptor (A) and donor (D) and determining the extent of energy transfer by the ratio of their emission amplitudes;

2) measuring the fluorescence lifetime of D;

3) measuring the rate of photobleaching of D;

4) measuring the anistropy of D and/or A; or 5) measuring the Stokes shift monomer:eximer fluorescence.

Other labels may be used, however, depending on the detection method employed to monitor the signal generated by the label. Labels may be attached in a number of ways, such as by direct labelling at suitable amino acids, such as cysteines or lysines, with chemical labels, or by fusion with a polypeptide label such as a fluorescent polypeptide. Techniques for labelling polypeptides and other molecules are generally known in the art and may be applied to the present invention.

The invention may be configured to exploit a number of non-fluorescent labels. In a first embodiment, the label is an enzyme which is capable of participating in an enzyme-substrate reaction which has a detectable endpoint. The enzyme may be cleaved into two or more components, such that upon binding of the binding partners to the protein the components reassemble to form a functional enzyme. Enzyme function may be assessed by a number of methods, including scintillation and photospectroscopy.

In a second embodiment, an enzyme is used together with a modulator of enzyme activity, such as an inhibitor or a cofactor. Binding of the enzyme and its inhibitor or cofactor results in modulation of enzymatic activity, which is detectable by conventional means.

In a third embodiment, which is a particular aspect of the enzymatic detection system, the invention is configured as a two-hybrid assay (Fields & Song, (1989), *Nature* 340, 245–6), in which two components of a transcription factor are used to label binding partners according to the invention. Assembly of the transcription factor results in activation of a transcription unit, with a resultant biological signal; a preferred biological signal is luciferase expression, which is easily assessed.

In any of the foregoing embodiments, assembly of the enzyme or transcription factor components is dependent upon the association of binding partners with the protein.

Generation of a Detectable Signal

Depending on the embodiment in question, signal useful in the present invention may be generated by a number of different labels. Preferred are fluorescent labels, and particularly preferred are fluorescent labels which participate in energy transfer (FRET).

FRET is detectable when two fluorescent labels which fluoresce at different frequencies are sufficiently close to each other that energy is able to be transferred from one label to the other. FRET is widely known in the art (for a review, see Matyus, 1992, *J. Photochem. Photobiol. B: Biol.*, 12: 323–337, which is herein incorporated by reference). FRET is a radiationless process in which energy is transferred from an excited donor molecule to an acceptor molecule; the efficiency of this transfer is dependent upon the distance between the donor an acceptor molecules, as described below. Since the rate of energy transfer is inversely proportional to the sixth power of the distance between the donor and acceptor, the energy transfer efficiency is extremely sensitive to distance changes. Energy transfer is said to occur with detectable efficiency in the 1–10 nm distance range, but is typically 4–6 nm for favourable pairs of donor and acceptor. Radiationless energy transfer is based on the biophysical properties of fluorophores. These principles are reviewed elsewhere (Lakowicz, 1983, *Principles of Fluorescence Spectroscopy*, Plenum Press, New York; Jovin and Jovin, 1989, *Cell Structure and Function by Microspectrofluorometry*, eds. E. Kohen and J. G. Hirschberg, Academic Press, both of which are incorporated herein by reference). Briefly, a fluorophore absorbs light energy at a characteristic wavelength. This wavelength is also known as the excitation wavelength. The energy absorbed by a fluorochrome is subsequently released through various pathways, one being emission of photons to produce fluorescence. The wavelength of light being emitted is known as the emission wavelength and is an inherent characteristic of a particular fluorophore. Radiationless energy transfer is the quantum-mechanical process by which the energy of the excited state of one fluorophore is transferred without actual photon emission to a second fluorophore. That energy may then be subsequently released at the emission wavelength of the second fluorophore. The first fluorophore is generally termed the donor (D) and has an excited state of higher energy than that of the second fluorophore, termed the acceptor (A). The essential features of the process are that the emission spectrum of the donor overlap with the excitation spectrum of the acceptor, and that the donor and acceptor be sufficiently close. The distance over which radiationless energy transfer is effective depends on many factors including the fluorescence quantum efficiency of the donor, the extinction coefficient of the acceptor, the degree of overlap of their respective spectra, the refractive index of the medium, and the relative orientation of the transition moments of the two fluorophores. In addition to having an optimum emission range overlapping the excitation wavelength of the other fluorophore, the distance between D and A must be sufficiently small to allow the radiationless transfer of energy between the fluorophores.

FRET may be performed either in vivo or in vitro. Proteins are labelled either in vivo or in vitro by methods known in the art. According to the invention, two coiled-coil domains comprised either by the same or by different polypeptide molecules are differentially labelled, one with a donor and the other with an acceptor moiety, and differences in fluorescence between a test assay, comprising a protein modifying enzyme, and a control, in which the modifying enzyme is absent, are measured using a fluorimeter or laser-scanning microscope. It will be apparent to those skilled in the art that excitation/detection means can be augmented by the incorporation of photomultiplier means to enhance detection sensitivity. The differential labels may comprise either two different fluorescent moieties (e.g., fluorescent proteins as described below or the fluorophores rhodamine, fluorescein, SPQ, and others as are known in the art) or a fluorescent moiety and a molecule known to quench its signal.

In a FRET assay of the invention, the fluorescent labels are chosen such that the excitation spectrum of one of the labels (the acceptor label) overlaps with the emission spectrum of the excited fluorescent label (the donor label). The donor label is excited by light of appropriate intensity within the donor's excitation spectrum. The donor then emits some of the absorbed energy as fluorescent light and dissipates some of the energy by FRET to the acceptor fluorescent label. The fluorescent energy it produces is quenched by the acceptor fluorescent label. FRET can be manifested as a reduction in the intensity of the fluorescent signal from the donor, reduction in the lifetime of its excited state, and re-emission of fluorescent light at the longer wavelengths (lower energies) characteristic of the acceptor. When the donor and acceptor labels become spatially separated, FRET is diminished or eliminated.

One can take advantage of the FRET exhibited by two binding partners labelled with different fluorescent labels, wherein one binding partner is linked to a donor and another to an acceptor label, in monitoring conformational state according to the present invention. Two distinct binding partners each capable of binding to a conformation of a protein may be differentially labelled with the donor and acceptor fluorescent protein moieties.

In a further embodiment, different labels may be applied to an number of first binding partners which are capable of binding to any one of a number of different conformations of a protein. Thus, in the same assay, it is possible to discern which one or more of the number of conformations is present by detecting FRET or another signal induced by the label(s) attached to the particular binding partner(s) which bind.

The means by which proteins are assayed for conformational change using fluorescent protein moiety labels according to the invention may be briefly summarised as follows:

Of two polypeptides which are capable of binding to a protein according to the present invention, one is labelled with a green fluorescent protein, while the other is preferably labelled with a red or, alternatively, a blue fluorescent protein. Useful donor: acceptor pairs of fluorescent proteins (see WO 97/28261) include, but are not limited to:

Donor: S72A, K79R, Y145F, M153A and T203I (excitation 395 nm; emission 511)

Acceptor: S659, S72A, K79R and T203Y (wavelengths not noted), or

T203Y/S65G, V68L, Q69K or S72A (excitation 515 nm; emission 527 nm).

An example of a blue:green pairing is P4-3 (shown in Table 1 of WO 97/28261) as the donor moiety and S65C (also of Table 1 of WO 97/28261) as the acceptor moiety. The polypeptides comprising coiled-coils are exposed to light at, for example, 368 nm, a wavelength that is near the excitation maximum of P4-3. This wavelength excites S65C only minimally. Upon excitation, some portion of the energy absorbed by the blue fluorescent protein moiety is transferred to the acceptor moiety through FRET if the two binding partners are in close proximity. As a result of this quenching, the blue fluorescent light emitted by the blue fluorescent protein is less bright than would be expected if the blue fluorescent protein existed in isolation. The acceptor moiety (S65C) may re-emit the energy at longer wavelength, in this case, green fluorescent light.

Advantages of fluorescent polypeptides constructed as fusions with fluorescent proteins include the greater extinction coefficient and quantum yield of many of these proteins compared with those of the Edans fluorophore. Also, the acceptor in such a construct or pair of constructs is, itself, a fluorophore rather than a non-fluorescent quencher like Dabcyl. Thus, the binding partners are both fluorescent but with different fluorescent characteristics.

Additional embodiments of the present invention are not dependent on FRET. For example the invention can make use of fluorescence correlation spectroscopy (FCS), which relies on the measurement of the rate of diffusion of a label (see Elson & Magde, (1974) Biopolymers 13:1–27; Rigler et al., (1992) in *Fluorescence Spectroscopy New Methods and Applications*, Springer Verlag, pp. 13–24; Eigen & Rigler, (1994) PNAS (USA) 91:5740–5747; Kinjo & Rigler, (1995) NAR 23:1795–1799).

In FCS, a focused laser beam illuminates a very small volume of solution, of the order of $10^{-15}$ l, which at any given point in time contains only one molecule of the many under analysis. The diffusion of single molecules through the illuminated volume, over time, results in bursts of fluorescent light as the labels of the molecules are excited by the laser. Each individual burst, resulting from a single molecule, can be registered.

A labelled molecule will diffuse at a slower rate if it is large than if it is small. Thus, binding partners bound to proteins will display slow diffusion rates, resulting in a lower number of fluorescent bursts in any given timeframe, whilst labelled binding partners which are not bound to proteins will diffuse more rapidly. Binding of binding partners according to the invention can be calculated directly from the diffusion rates through the illuminated volume.

Where FCS is employed, rather than FRET, it is not necessary to label more than one binding partner. Preferably, a single binding partner is labelled.

A further detection technique which may be employed in the method of the present invention is the measurement of time-dependent decay of fluorescence anisotropy. This is described, for example, in Lakowicz (1983) *Principles of Fluorescence Spectroscopy*, Plenum Press, New York, incorporated herein by reference. See, for example, page 167.

Fluorescence anisotropy relies on the measurement of the rotation of fluorescent groups. Larger protein rotate more slowly than smaller binding partners, allowing the formation of protein:binding partner associations to be monitored.

In an alternative embodiment, particularly where the invention is configured as an immobilised sensor with the protein covalently or non-covalently bound to a solid phase support, the signal generation method use may be more diverse. In this configuration, because it is possible to wash away or otherwise remove unbound binding members, only a single label is required.

The label may be optical, for example fluorescent, an absorptive coloured particle or a dye, radioactive, such as may be applicable for use in a scintillation proximity assay, or a scintillation emulsion, enzymatic, such as a glucose oxidase sensor or other redox system or an immobilised chemical cascade, or based on mass, as might be applicable in a surface plasmon resonance-based assay, in which case either the protein or the binding partner must be of high molecular weight.

In a still further embodiment, the detection system may be based on an enzymatic approach, for example involving the reconstitution of an enzyme by binding of two binding partners to the protein, which binding partners are associated with domains of an enzyme which reassociate to form an active enzyme. The enzyme itself may be any enzyme which is capable of catalysing a reaction having a suitable detectable end-point, such as a colorimetric assay, an absorbance-based assay, a fluorescence-based assay, a radioactive assay or a coupled enzyme reaction. In an alternative embodiment, the binding partners may be associated with an enzyme and an inhibitor therefor; in this configuration, the binding partners are induced to associate by binding of one or both of them to the protein, and the enzyme activity thus decreases. Moreover, the invention may be configured as a two-hybrid assay, as described above.

The invention is further described below, for the purposes of illustration only, in the following Examples.

EXAMPLES

Example 1

Measuring the Ligand Bound Conformation of Calmodulin

Calmodulin is isolated from natural sources or expressed in cells in culture. Abundant sources of calmodulin include brain and testes of mammalian species. Calmodulin is isolated from bovine testes according to the method of Gopalakrishna & Anderson (1982, Biochem. Biophys. Research Communications 104, 830–836).

In order to identify a binding partner capable of binding to calcium complexed as well as free calmodulin, a phage peptide library is panned with immobilised calmodulin both in the presence and absence of calcium. In a first panning run, conducted in a calcium-free buffer, binders are retained which bind to calcium-free calmodulin. These binders are then eluted and passed over the immobilised calmodulin a second time, in the presence of calcium ions. Binders which are retained a second time are able to bind calcium-complexed and uncomplexed calmodulin. A peptide is selected from the remaining binders, and designated binding partner A. Thus, binding partner A interacts with calmodulin irrespective of the presence or absence of ligand ($Ca^{2+}$ions).

In order to isolate a further binding partner which will bind only to calcium-complexd calmodulin, the procedure is repeated, except that the second pan is performed using non-binders eluted from the first calcium-free pan. The resulting binding partner, binding partner B, interacts with calmodulin only when calmodulin is ligand bound ($Ca^{2+}$ion bound form).

The binding partners are then labelled using a method adapted from one known in the art (Hermanson, 1996, *Bioconjugate Techniques*, Academic Press). 20 mM fluorescein iodoacetamide (FAM) in DMSO and 0.23 mM peptide in 20 mM TES buffer, pH 7.0 are prepared. These are mixed in a molar ratio of 0.9:1 (Partner A:label) and incubated at 4° C. in the dark for a minimum of 2 hours. This method is also applied to labelling partner B with rhodamine, and good labelling is obtained using rhodamine iodoacetamide at a ratio of 0.9:1. Labelling is assessed by reverse phase HPLC (C18 column; solvent A: $H_2O$/0.1% TFA; solvent B: acetonitrile/0.1% TFA) and MALDI-TOF mass spectrometry. Binding partners AF and BR labelled with fluorescein and rhodamine respectively are thus generated.

A range of assay solutions is prepared, containing the following components (at final concentrations): Histidine buffer pH 7.0 (50 mM), KCl (120 mM), $MgSO_4$ (1 mM) EGTA (1 mM) and $CaCl_2$ (0.1–10 mM). This generates ionised $Ca^{2+}$ ion concentrations ranging from ~1 nM to 9 mM, and the precise $Ca^{2+}$ ion concentration can be calculated using computer programs in the public domain (EQCAL, Biosoft, Cambridge, UK). Calmodulin at a final concentration of 1 $\mu$M is added to each assay which differs in ionised $Ca^{2+}$ concentration (above), along with 1 $\mu$M donor fluorophore labelled binding partner AF (Fluorescein labelled A: concentration equal to that of calmodulin). Each sample is excited individually at 490 nm and a fluorescence emission spectrum from 505 nm to 650 nm is recorded. A peak of fluorescein fluorescence at 515 nm is observed in each case. Binding partner BR is added to a final concentration of 1 $\mu$M (equal to the calmodulin concentration, above). The fluorescence emission spectrum is recorded again as above. In these samples two emission maxima are observed; the donor at 515 nm and the acceptor at 580 nm. The proportion of ligand bound calmodulin is reflected in the ratio of these two emission maxima. The 515 nm signal decreased and the 580 nm maxima increased concomitant with the appearance of the ligand bound form of calmodulin.

A graphical plot of the fluorescence emission ratio (580/515 nm) vs. ionised $Ca^{2+}$ concentration displays the appearance of the ligand bound form of calmodulin and the saturation of that receptor with ligand at ~10 $\mu$M $Ca^{2+}$. Such a plot can be used as a calibration curve to measure the ligand concentration under standard conditions where the ligand ($Ca^{2+}$ in this case) content of a sample is unknown.

Example 2

Many proteins are subject to post-translational modification, and there are many known examples where this modification leads to changes (stimulation or inhibition) in the catalytic activity of the modified protein. Examples of such modification include phosphorylation, dephosphorylation, prenylation, proteolysis etc.

Posttranslational modification of the target substrate can also be exhibited in many interactions such as homo/hetero dimerisation, oligomerisation of the modified protein or binding to other proteins thus resulting in a more active or inactive state. The modification can also lead to simple conformational changes of the modified substrate whereby by the new configuration of the protein reflects the activity or inactivity of the protein.

The changes in the conformation of the modified protein can be exploited to directly measure the activity of the modifying enzyme. For example phosphorylation/dephosphorylation of proteins which result in the addition or removal of a phosphate moiety to or from the target protein may lead to a conformational change associated with this modification.

Therefore assays can be configured to distinguish and discriminate between the unmodified and modified states of the target protein which will report the activity of the modifying enzyme.

Solution Phase Assay Configurations:

FRET Measurement of Protein Kinase C Activity by the Detection of the Conformational Changes in the Substrate $p47^{phox}$.

One way of measuring the activity of the post-translational modifying enzyme such as a kinase or phosphatase is to construct a peptidic partner that will bind the substrate whether it is modified or unmodified (i.e. in both conformation states). A second peptide partner which can bind to the substrate only if it is modified is then constructed. This peptide can be designed to bind to a newly exposed surface on the modified protein based on specific sequence recognition or identified by phage display technology for an unknown binding site. These two peptides can be labelled with appropriate fluorophores (e.g. fluorescein and rhodamine) which will exhibit Fluorescence Resonance Energy Transfer (FRET) when they are in close proximity.

The concept of the assay is that when the substrate is unmodified, only the first peptide will bind. Upon modification such as by a kinase or a phosphatase the substrate undergoes a conformational change leading to unmasking of a binding motif which will bind the second peptide. Therefore the activity of the modifying enzyme can be measured by monitoring FRET between the two bound, labelled peptides (See FIG. 1).

$p47^{Phox}$ is a cytosolic component of NADPH oxidase. In phagocytes the oxidase plays an important role in the host defense against microbial infections by catalysing the oxidation of NADPH and reduction of molecular oxygen to superoxide ($O_2^-$), a reactive oxygen species critical for the host defense against infectious diseases.

In resting cells the enzyme is inactive, but in response to external stimuli $p47^{phox}$ is phosphorylated by protein kinase C leading to its translocation to the membrane and the initiation of the oxidase activity by binding to other oxidase components such as $p22^{phox}$ and $p67^{phox}$.

The human $p47^{phox}$ is 390 amino acids long constituting 4 different domains, the N-terminal phox homology domain (1–128aa) two SH3 domains (154–219 and 223–286 aa respectively) and a C-terminal domain which encompasses PKC and MAPK phosphorylation sites and a proline rich motif.

Figure 2:
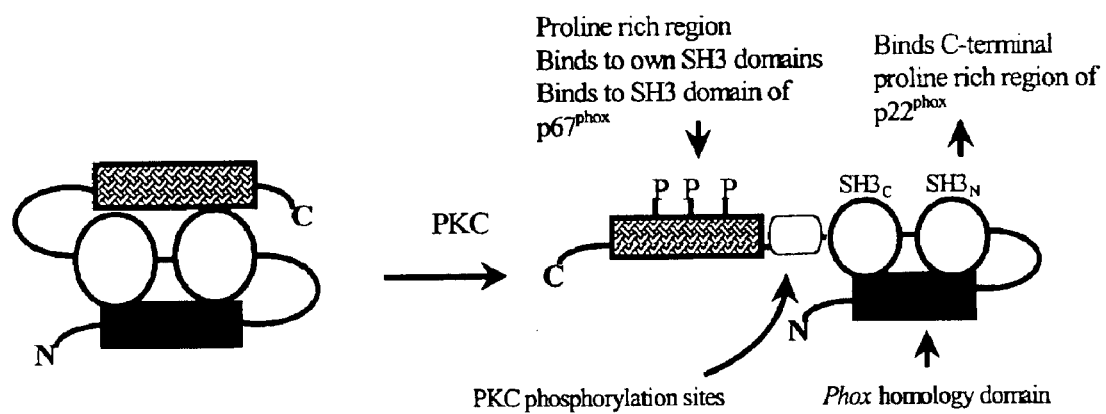
FIG. 2. PKC-induced conformational change in the structure of p47$^{phox}$.

Phosphorylation of $p47^{phox}$ by PKC at several serine residues such as those at positions 303, 304 and 328 causes a large conformational change in the substrate which leads to unfolding of the structure and the unmasking of different binding motifs such as the tandem SH3 domains. These domains are known to bind proline rich sequence motifs. In its inactive state the C-terminal domain of $p47^{phox}$ makes intermolecular interactions with its SH3 domains. These interactions are disrupted by phosphorylation, exposing both SH3 domains. The N-terminal SH3 then binds to the proline rich C-terminal region of p22$^{phox}$ whereas the C-terminal proline rich region interacts with the C-terminal SH3 domain of p67$^{phox}$ (FIG. 2).

This example can be used to configure assays where the activity of PKC can be measured by monitoring the conformational changes in the substrate.

Plasmid Construction:

DNA fragments encoding the full length of p47$^{phox}$ (amino acids 1–390) is amplified from a cloned cDNA encoding human p47$^{phox}$ (GenBank Accession No. NM_000265) by PCR using the primers shown below and ligated to pET 28 (Novagen) or pGEX-2T (Amersham Pharmacia Biotech) vectors.

p47$^{phox}$ Forward Primer-GGGCATGGGGAGAGCTTCATCC p47$^{phox}$ Reverse Primer-GGGGAAGGCTGACGGCAGACGCCAGC For purification purposes DNA encoding p47$^{phox}$ is inserted in the vector downstream of a hexa-His tag or GST tag. For fluorescent labelling purposes DNA encoding a coiled coil peptide (peptide 1, LMRQLQDEVEELEQENWHLQNEVARLLREVQCLEAEV) is inserted in the vector downstream of p47$^{phox}$. This technique can be used to fuse monomers of coiled coils specifically on either N- or C-termini of the protein. The partner coil peptide is chemically synthesised and labelled with a chemical fluorophore. The protein-coil fusion is labelled by mixing with the partner, labelled peptide as described below.

Protein Expression and Purification:

Fresh transformants of p47$^{phox}$ coiled coil pET-28a in BRL (DE3) and p47$^{phox}$-GFP pET-28a in BRL (DE3) pLysS are used to inoculate 3 ml LB/kanamycin (100 μg/ml). The starter cultures are incubated overnight at 37° C. with shaking. From these starter cultures 1 ml is used to inoculate 400 ml Terrific Broth/kanamycin (100 μg/ml) in a 2 L, baffled flask. Cultures are incubated at 37° C. with constant shaking for approximately 5 hrs until the OD600 nm have reached 0.5 Abs units. At this point cultures are induced by the addition of 1 mM IPTG. The cultures are then left incubating at room temperature overnight with gentle shaking on a benchtop rotator.

Bacteria are harvested by centrifugation at 3000 rpm for 20 mins. The bacterial pellet is resuspended in 25 ml lysis buffer (50 mM phosphate pH 7.0, 300 mM NaCl, 2% Proteinase inhibitor cocktail (Sigma), 0.75 mg/ml Lysozyme). Lysis of the resuspended cells is initiated by gentle stirring for 1 hr at room temperature. The partially lysed mixture is subjected to 2 cycles of freeze thawing in liquid nitrogen. Finally the cells are sonicated on ice using a 10 mm probe at high power. Sonication is performed on a pulse setting for a period of 3 min. The crude lysate is then centrifuged at 15000 rpm for 30 mins to remove cell debris.

Recombinant proteins can then be purified as follows:

His-tagged proteins, for example the His$_6$-p47$^{phox}$, His$_6$-p47$^{phox}$-coiled coil and His$_6$-p47$^{phox}$-GFP constructs, are typically purified on metal affinity resins such as TALON (CLONTECH Laboratories, Inc.). Proteins are bound to the resin in a batchwise manner by gentle shaking at room temperature for 30 min. Non-His tagged proteins are removed by washing the resin at least twice with 10× bed volume of wash buffer (50 mM sodium phosphate pH 7.0, 300 mM NaCl, 5 mM fluorescence-blank imidazole). The washed resin is loaded into a 2 ml column and the bound proteins released with elution buffer (50 mM sodium phosphate pH 7.0, 300 mM NaCl, 150 mM florescence-blank imidazole). Protein containing samples are then snap frozen in liquid nitrogen and stored at −80° C. in the presence of 10% glycerol.

GST-tagged constructs can be purified on glutathione sepharose 4 fast flow pre-packed columns (Amersham pharmacia biotech). The sonicate of cells expressing the target protein is bound to the matrix in 20 mM phosphate buffer pH 7.3 containing 150 mM NaCl. The protein can then be eluted with 10 mM reduced glutathione in 50 mM Tris-HCl pH 8.0.

Fluorescent Labelling of p47$^{phox}$.

Figure 3:
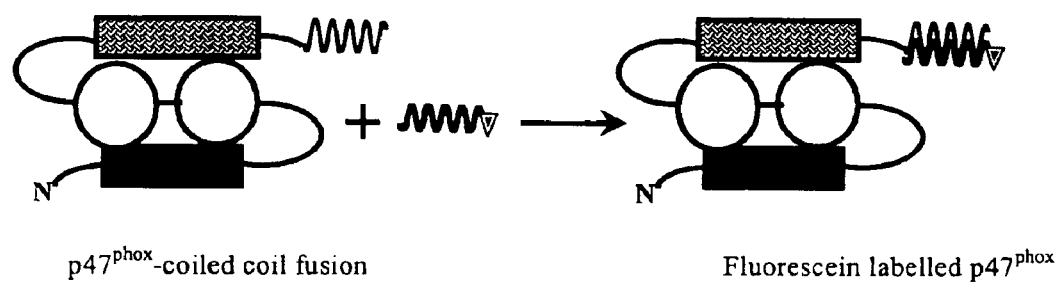
FIG. 3. Labelling of p47$^{phox}$-coiled coil fusion protein with a specific coiled oil partner.

The purified protein constructs are labelled with a fluorescent tag as follows:

Coiled Coil Labelling:

In the case where the p47$^{phox}$ protein is fused to a coiled coil (peptide sequence 1), labelling is achieved by the attachment of a pre-labelled heterodimer coiled coil partner (peptide 2, RMRQLEDRVEELREQNWHLANQVARLRQRVCELKARV) as shown in FIG. 3.

Initially peptides are labelled with fluorescein in 100 μl of 10 mM TES buffer pH 7.0 for thiol directed or in 200 mM Bicarbonate buffer pH 8.5 for amine directed chemistries. Excess label will be removed by dialysis.

Labelling of the substrate (p47$^{phox}$) is then achieved by mixing with equimolar concentrations of a labelled coiled coil partner (peptide 2).

The efficiency of labelling is tested by monitoring the increase in fluorescence polarisation as indication of peptide binding to the protein.

In Vitro FRET Assays for the Detection of PKC Activity.

With the present example there are at least two options for performing FRET assays for the detection of PKC activity, by monitoring the conformational changes of the substrate as a result of phosphorylation.

Figure 4:
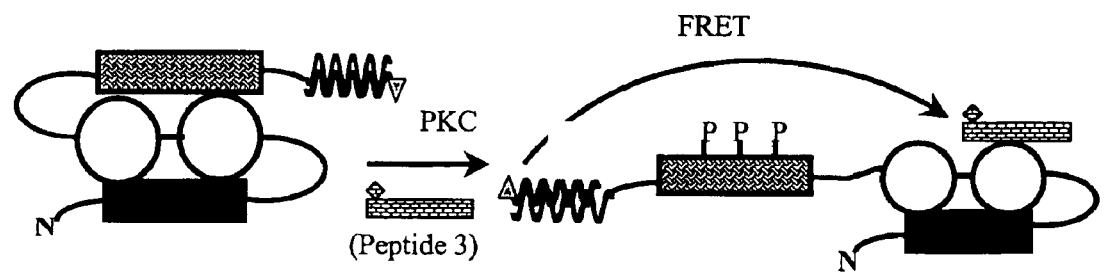
FIG. 4. Phosphorylation dependent conformational change and binding of partner peptide causing FRET.

Assay 1 p47$^{phox}$ protein (0.5 μg) labelled with fluorescein through coiled coil attachment as described above is incubated for 2–5 min in 100 μl of 50 mM Tris-HCl buffer pH 7.4, 1 mM ATP, 10 mM Mg(OAc)$_2$ and 0.5 mM Ca$_2$Cl. In the presence of peptides 3 or 4 (KQPPSNPPPRPPAE or CQRSKPQP AVPPRP) labelled with rhodamine (these peptides are derived from the binding protein partner p22$^{phox}$, another component of NADPH oxidase or from the C-terminal segment of p47$^{phox}$ and binds only if the substrate has undergone conformational change as a result of phosphorylation—see FIG. 4). Phosphorylation is then initiated by the addition of 50 ng of PKC. The enzymatic activity is monitored by exciting the sample at 490 nm and measuring the decrease in the fluorescein emission at 520 nm due to FRET.

Assay 2

In many other known examples, conformational change studies make use of the changes in tryptophane fluorescence as an indication of increased or decreased hydrophobicity as a result of modification. Where this is the case, assays can be configured to monitor the activity of the modifying enzyme by using tryptophane 193 (this W residue was shown to be critical for both p22$^{phox}$ binding and oxidase activity) as a donor fluorophore. The acceptor can be peptides 3 or 4 which is labelled with a Dansyl fluorophore that can be used as an acceptor for tryptophane fluorescence, thus measuring FRET in the same manner as described above.

Fluorescence Polarisation Assay for the Detection of Conformational Changes Due to Phosphorylation.

Assay 3

In this type of assay one label is sufficient to report on the modification and association or dissociation of macromolecules due to modification. The technique is based on measurements of the rate of tumbling and rotation of macromolecules in solution. Small molecules rotate fast causing low polarisation whereas large molecules rotate slower yielding high polarisation.

Figure 5:
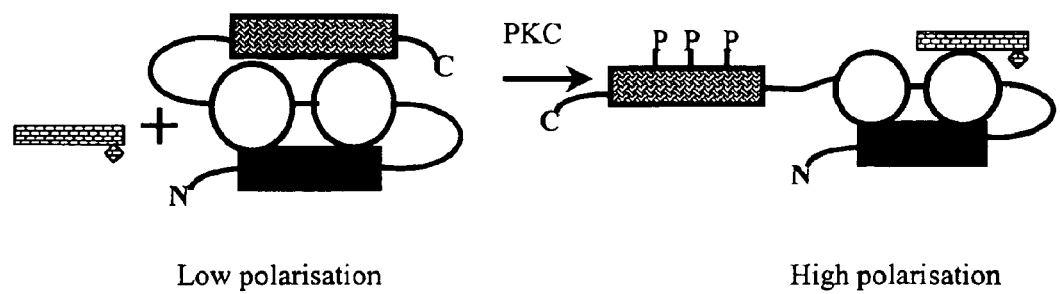
FIG. 5. Phosphorylation dependent conformational change and binding of a peptide partner measured by fluorescence polarisation.

The application of FP to measure conformational changes induced by modification of the substrate as a result of phosphorylation requires one labelled peptide partner that in the present example will recognise and bind only to the modified conformation of the substrate (FIG. 5).

p47$^{phox}$ protein (0.5 µg) in 100 µl of 50 mM Tris-HCl buffer pH 7.4, 1 mM ATP, 10 mM Mg(OAc)$_2$ and 0.5 mM CaCl$_2$ is incubated for 5 min with equimolar concentration of a fluorescein labelled peptide 3 (binds to the N-terminal SH3 only when p47$^{phox}$ is phosphorylated). The phosphorylation is initiated by the addition of 50 ng of PKC and the enzymatic activity monitored by measuring the increase in FP due to peptide binding to the modified substrate. The sample was excited at 490 nm and the emission was measured at 520 nm).

Immobilised Assay Configurations.

Immobilised Assay for the Detection of Post-translational Modification Induced Conformational Change.

Immobilised assays can be configured to measure the activities of post-translational modifying enzymes that result in conformational changes.

The advantages of these types of assays lie in the ability to measure the activity of a specific enzyme in a complex mixture, cell extracts as well as complex samples such as body fluids.

Assay 4

Figure 6:
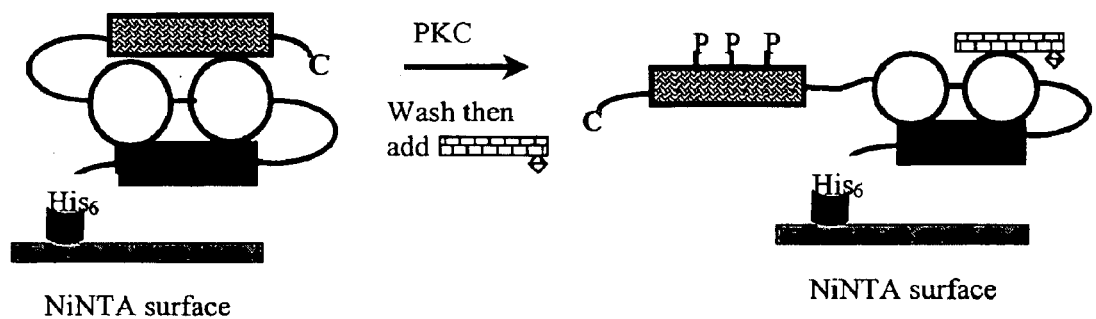
FIG. 6. Detection of PKC-induced conformational change of immobilised p47$^{phox}$.

In these assays the protein p47$^{phox}$ tagged with either GST or His$_6$ (as described above) is immobilised Ni-NTA or GSH-coated 96 well plates in 50 mM Tris-HCl pH 7.4, 100 mM NaCl, 0.005% Tween and 1% bovine serum albumin. The protein is allowed to bind for up to 1 hour at room temperature. Unbound protein is removed by washing the plate 3 times with the same buffer. 100 µl of 50 mM Tris-HCl, 1 mM ATP, 10 mM Mg(OAc)$_2$ and 0.5 mM CaCl$_2$ is added and phosphorylation is initiated by the addition of 10 ng PKC. When the reaction is over, the plate is washed 3 times with the buffer followed by the addition of the partner peptide (peptide 3) which will bind only to the phosphorylated, modified conformation. Excess peptide is washed away and the extent of binding is detected by measuring fluorescence intensity of the label e.g. fluorescein emission at 520 nm by exciting at 485 nm (FIG. 6).

Alternatively the assays can be configured to measure the conformational changes by the immobilisation of the binding partner peptide and monitoring the enzyme activity by the fluorescence of captured protein.

Assay 5

Figure 7:
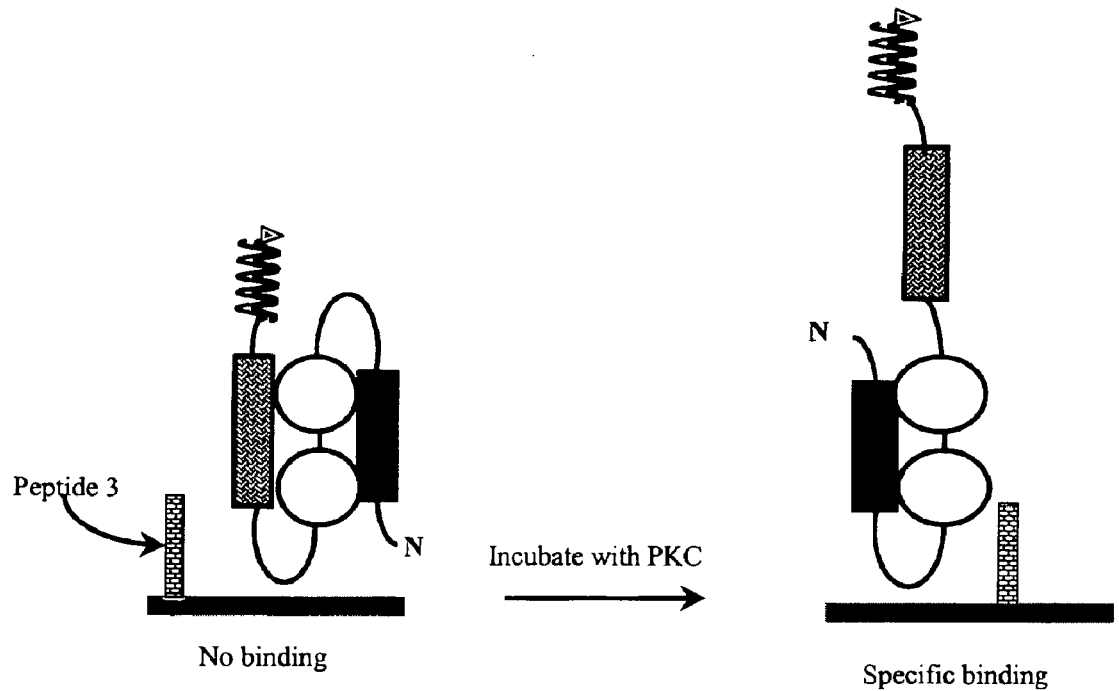
FIG. 7. Detection of PKC-induced conformational change of p47$^{phox}$ via the immobilisation of peptide 3.

In this format, peptide 3 synthesised with a hexa-His tag or biotin as an anchoring moiety is immobilised to a solid support such as Ni-NTA or Streptavidin-coated 96 well plates in appropriate buffer under conditions described above. Excess, unbound peptide is washed 3 times with buffer and the bound sample is reconstituted in 100 µl of 50 mM Tris-HCl pH 7.4, 1 mM ATP, 10 mM Mg(OAc)$_2$ and 0.5 mM CaCl$_2$. The substrate (p47phox) labelled with a coiled coil dimer as in example 1 is then added and phosphorylation is initiated by the addition of 10 ng PKC. When the reaction is over the plate is washed 3 times with buffer and the degree of phosphorylation is measured by the extent of binding of the modified p47$^{phox}$ substrate to the immobilised peptide (FIG. 7).

Simultaneous Assay for the Detection of Post-translational Modifying Enzymes that Result in a Conformational Change.

Assay 6

The concept of immobilised assay described above can be applied to configure assays to measure the activities of multiple post-translational modification enzymes that lead to conformational changes in their substrates in a complex sample.

Coiled coil labelling of proteins can be adopted to specifically label multiple targets each with a specific pair of heterodimeric coiled coils. The partner coil of each pair is then specifically labelled with a chemical fluorophore as described above yielding proteins labelled with different fluorophores.

Figure 8:
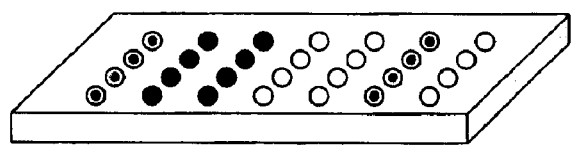
FIG. 8. Configuration of multiplexed assay format for the detection of PTME-induced conformational change.

A common peptide partner or a specific partner for each target protein is immobilised o a solid support as described in the examples above. The sample (eg. a cell lysate) is then added to the immobilised array of specific binding partners and the activities of unlimited modifying enzymes are monitored by the extent of binding of their respective substrates (FIG. 8).

Example 3

Assays for the detection of phosphorylation dependent conformational change of Src kinase.

Src is a member of non-receptor tyrosine kinase family, it is the first proto-oncogene demonstrated to have a tyrosine kinase activity and has been shown to be involved in many aspects of cell growth, differentiation and metabolism. It is a highly attractive target for multiple disease states including inflammation, cancer and immune responses.

Src family kinases have a common domain organisation with each segment designated as a Src homology (SH) region. The N-terminal region (50–70 amino acids) a unique segment for each protein family member which contains myristylation and membrane localisation signals is designated as SH4. The SH3 (50–60 amino acids) plays an important role in mediating protein-protein interactions in cellular signals, this domain binds to proline rich motifs. The SH2 domain (ca. 100 amino acids) also mediates protein-protein interactions via binding to specific phosphotyrosine containing motifs and the SH1, the kinase catalytic domain (280 amino acids) which contains an autophosphorylation site. In addition there is a small C-terminal segment which contains a highly conserved tyrosine residue that has a critical role in the regulation of the kinase activity.

In resting cells, when this critical tyrosine is phosphorylated by C-terminal Src Kinase (CSK), the C-terminal segment makes intramolecular interactions with the SH2 domain rendering the enzyme inactive. In addition to these interactions the SH3 contributes to the down regulation of the kinase activity by association with a proline containing peptide segment that links the SH2 with the kinase domains. Upon dephosphorylation of the C-terminal tyrosine residue, the catalytic domain becomes open rendering the enzyme active.

Taking this example, FRET based assays are configured to detect the phosphorylation or dephosphorylation dependent conformational changes that occur in the protein domains, as a result of protein modifying enzyme activity.

The assay is configured in a way such that the full length Src is expressed as a fusion protein with a coiled coil monomer for the purpose of labelling whereby a partner coiled coil peptide is chemically synthesised and labelled with a chemical fluorophore (see Example 3 for details). Upon dimerisation Src becomes specifically labelled with the fluorophore.

A second peptide that will only bind to the modified substrate is chemically synthesised and labelled with a second chemical fluorophore and which will exhibit FRET with the first fluorophore when the substrate is modified.

Plasmid Construction

DNA fragments encoding the full length of Src kinase (amino acids 1–536) are amplified from a cloned cDNA encoding v-Src (GeneBank accession number NP_005408) by PCR using the following primers:

```
Forward primer GGGCATATGGGTAGCAACAAGAGC

Reverse primer GGGAATTCTGAGGTTCTCCCCGG
```

The DNA is then ligated to pET 28 vector (Novagen). For purification purposes DNA encoding v-Src is inserted in the vector downstream of a $His_6$ tag. For fluorescent labelling purposes, DNA encoding a coiled coil peptide (peptide1, LMRQLQDEVEELEQENWHLQNEVARLLREVQCLE AEV) is inserted in the vector downstream of v-Src. This technique is used to fuse monomers of coiled coils specifically on either N- or C-termini of the protein. The partner coil peptide is chemically synthesised and labelled with a chemical fluorophore such as fluorescein. The protein-coil fusion is labelled by mixing with the coil partner peptide labelled as described below.

Alternatively, DNA encoding green fluorescent protein (GFP) or one of its variants such as blue fluorescent protein (BFP) purchased from Quantum Biotechnologies Inc. is inserted downstream of Src to create a Src-GFP fusion.

Protein Expression and Purification:

Proteins were expressed labelled and purified as in Example 2.

Assays for CSK Activity.

In vitro FRET assays for the detection of CSK activity via phosphorylation dependent conformational change in Src.

With the present example FRET assays for the detection of CSK activity are configured to monitor the conformational changes of the substrate as a result of phosphorylation.

Assay 1 v-Src protein (0.5 µg) labelled with fluorescein through coiled coil attachment as described above is incubated for 2–5 min in 100 µl of 50 mM Tris-HCl buffer pH 7.4, 10 mM DTT, 200 µg/ml BSA, 1 mM ATP and 4.0 mM $MnCl_2$. In the presence of peptide 4 (KAVPLARRPLPPLP) labelled with rhodamine at the K residue in 200 mM bicarbonate buffer pH 8.5 (this peptide is shown to bind with high specificity to SH3 domain of Src). An alternative peptide can also be used in combination with the coiled coil labelled Src (peptide 5, CPTSKPQTQGLAK). This peptide is derived from Src SH2-kinase domain linker segment which is known to bind the SH3 domain when Src is in the inactive form. These two peptides peptide 4 or 5) will therefore bind only when Src is in the active unphosphorylated form and exhibit FRET. Phosphorylation is then initiated by the addition of 10–50 ng of CSK and the enzymatic activity is measured monitoring the loss of FRET. Exciting the sample at 490 nm and measuring the increase in the fluorescein emission at 520 nm due to the change in the conformation of Src and dissociation of peptide partners.

Fluorescence Polarisation Assays for the Detection the Conformational Changes in Src Following its Phosphorylation by C-terminal Src Kinase (CSK).

Assay 2

In this assay, One label is sufficient to report on the phosphorylation dependent conformational change in Src and therefore the enzymatic activity of CSK.

Active v-Src protein (0.5 µg) is incubated for 2–5 min in 100 µl of 50 mM Tris-HCl buffer pH 7.4, 10 mM DTT, 200 µg/ml BSA, 1 mM ATP and 4.0 mM $MnCl_2$. In the presence of peptide 4 (KAVPLARRPLPPLP) labelled with fluorescein at the K residue in 200 µl of 200 mM bicarbonate buffer pH 8.5 at 1:1 (label:peptide) ratio (this peptide is shown to bind with high specificity to SH3 domain of Src). An alternative peptide (peptide 5, CPTSKPQTQGLAK) is derived Src SH2-kinase domain linker segment which is known to bind the SH3 domain when Src is in the inactive form. These two peptides (peptide 4 or 5) will therefore bind only when Src is the active unphosphorylated form. Phosphorylation is then initiated by the addition of 10–50 ng of CSK and the enzymatic activity is measured by monitoring the decrease in the peptide-fluorescein polarisation at 520 nm (exciting the sample at 490 nm) due to the dissociation of the peptide from the Src.

Immobilised Assay for the Detection of Phosphorylation Dependent Conformational Change of Src, and Assay of CSK Activity.

Assay 3

In these assays the Src protein (0.5 µg) tagged with $His_6$ (as described above) is immobilised to Ni-NTA coated 96 well plates in 50 mM Tris-HCl pH 7.4, 100 mM NaCl, 0.005% and 1% BSA. The protein is allowed to bind for up to 1 hour at room temperature. Excess, unbound protein is removed by washing the plate 3 times with the same buffer. 100 µl of 50 mM Tris-HCl buffer pH 7.4, 10 mM DTT, 200 µg/ml BSA, 1 mM ATP and 4.0 mM $MnCl_2$ was then added and phosphorylation is initiated by the addition of 10–50 ng CSK. When the reaction is over, the plate is washed 3 times with the buffer followed by the addition of the partner peptide (peptides 4 or 5). Excess peptide is washed off and the extent of binding is detected by measuring fluorescence intensity of the label e.g. fluorescein emission at 520 nm by exciting at 485 nm.

Assay 4

Alternatively the Src-coiled coil fusion protein is immobilised to Streptavidin-coated plates through biotinylation of the partner coiled coil (peptide 2). Initially the biotinylated coiled coil monomer is immobilised to streptavidin plates in a buffer containing 50 mM Tris-HCl pH 7.4, 100 mM NaCl, 0.005% and 1% BSA. Excess peptide is washed off, then the coiled coil tagged Src (0.5 µg) is added to the immobilised coiled coil monomer in 50 mM Tris-HCl pH 7.4, 100 mM NaCl, 0.005% and 1% BSA. The protein is allowed to bind for up to 1 hour at room temperature. Excess, unbound protein is removed by washing the plate 3 times with the same buffer. 100 µl of 50 mM Tris-HCl buffer pH 7.4, 10 mM DTT, 200 µg/ml BSA, 1 mM ATP and 4.0 mM $MnCl_2$ is then added and phosphorylation is initiated by the addition of 10–50 ng CSK. When the reaction is over, the plate is washed 3 times with the buffer followed by the addition of the partner peptide (peptides 4 or 5). Excess peptide is washed off and the extent of binding is detected by measuring fluorescence intensity of the label e.g. fluorescein emission at 520 nm by exciting at 485 nm.

The CSK activity as well as specific inhibition profiles is measured by measuring the extent of bound labelled peptide partner (peptide 4 or 5). e.g. full binding means no activity or fully inhibited CSK whereas no peptide binding (capture) reflects phosphorylated Src, therefore reporting full activity or lack of inhibition.

Example 4

Detection of conformation change of Erk2 protein kinase due to phosphorylation, using fluorescent, peptidic binding partners.

The MAP kinase isoforms ERK1 and ERK2 mediate key events throughout the cell and phosphorylate transcription factors, cytoskeletal proteins and other protein kinases and enzymes. The activity of MAP kinases is tightly controlled by dual phosphorylation (Ahn et al., 1991, J. Biol. Chem. 266: 4220–4227; Payne et al., 1991, EMBO J. 10: 885–892; Robbins et al., 1993, J. Biol. Chem. 268: 5097–5106). Phosphorylation leads to over 1000-fold activation of ERK1 and ERK2. Activation of ERK2 by dual phosphorylation can be monitored by the binding of fluorescent peptides to the active, or inactive forms. Such peptides can be derived from regions of intramolecular interaction observed in the crystal structures of the different conformations of the kinase.

Source of ERK2, Phosphorylated and Non-phosphorylated and MEK1

Active murine ERK 2 and unactivated murine ERK 2 are from Upstate Biotechnologies. MEK1 from rabbit is also from Upstate Biotechnologies.

Cloning and Expression of ERK2 From Rat, Labelling With Fluorophore ERK2-FJ:

Primers are designed based on the published Erk2 sequence (Genbank accession number M64300). The kinase (amino acids 1–358) is cloned by PCR using the following oligo-nucleotides:

```
Forward primer:  GGCATATGGCGGCGGCGGCGGCGGCGGG

Reverse Primer:  CCCATTGTAGATCTGTATCCTGGC
```

The resultant PCR fragment is digested with NdeI and MfeI and ligated into pFS101 which had been digested with NdeI and EcoRI. This positions the DNA encoding the ERK2 kinase N-terminal and in-frame to DNA encoding a coiled-coil peptide sequence derived from Fos/Jun:

LMRQLQDEVEELEQENWHLQNEVARLLREVQ CLEAEV

The DNA encoding the ERK2-FJ fusion protein is under the control of the T7 promoter for expression in E. coli.

Fresh transformants of ERK2 expressing plasmid in BRL (DE3) pLysS are used to inoculate 3 ml LB/kanamycin (100 µg/ml). The starter cultures is incubated overnight at 37° C. with shaking. From these starter cultures 1 ml is used to inoculate 400 ml Terrific Broth/kanamycin (100 µg/ml) in a 2 L, baffled flask. Cultures are incubated at 37° C. at 200 rpm for approximately 4 hr until the $OD_{600nm}$ has reached 0.5 Abs units. At this point cultures are induced by adding IPTG to a concentration of 1 mM and further incubated at 37° C. for 4 hrs.

Bacteria are harvested by centrifugation at 3000 rpm for 20 min. The bacterial pellet is resuspended in 25 ml lysis buffer (50 mM phosphate pH 7.0, 300 mM NaCl, 2% Proteinase inhibitor cocktail (Sigma), 0.75 mg/ml Lysozyme). Lysis of the resuspended cells is initiated by gentle stirring for 30 min at room temperature. Nonidet P-40 is added to a final concentration of 1% and lysis is continued for a further 20 min at room temperature. The partially lysed mixture was subjected to 3 cycles of freeze thawing in liquid nitrogen. Finally the cells are sonicated on ice using a 10 mm probe at high power. Sonication is performed on a pulse setting for a period of 4 min. The crude lysate is centrifuged at 15000 rpm for 30 min to remove cell debris. Hexa-His tagged proteins are purified from the cleared lysate using TALON® resin (Clontech). Proteins are bound to the resin in a batchwise manner by gentle shaking at room temperature for 30 min. Non-His tagged proteins are removed by washing the resin at least twice with 10× bed volume of wash buffer (50 mM sodium phosphate pH 7.0, 300 mM NaCl, 5 mM fluorescence-blank imidazole). The washed resin is loaded into a 2 ml column and the bound proteins are released with elution buffer (50 mM sodium phosphate pH 7.0, 300 mM NaCl, 150 mM florescence-blank Imidazole). Elution is normally achieved within 5 ml. Purified proteins are stored at −80° C. after snap freezing in liquid nitrogen in the presence of 10% glycerol.

The corresponding synthetic Fos/Jun polypeptide partner that forms the coiled-coil pair with ERK2-Fos/Jun was designed and prepared:

RMRQLEDRVELREQNWHLANQVARLRQRVCE LKARV

Peptide domains can be specifically labeled on amine or thiol groups with chemical fluorophores such as fluorescein or rhodamine. Fluorophores with thiol or amine reactive chemistries are readily available from commercial sources such as Molecular Probes. These fluorophores can be conjugated to peptides under mild conditions (e.g. 20 mM TES pH 7 for thiol directed labeling, or 200 mM sodium bicarbonate pH 8.3 for amine directed labelling, using 230 µM peptide in the presence of 200 µM label).

The Fos/Jun polypeptide partner is labelled with fluorescein through amine directed labeling. Purified ERK2-FJ is mixed with the polypeptide partner and the mixture monitored by FP to detect coiled-coil formation between the F/J peptides, resulting in Erk2 labelled with fluorescein.

Alternatively, the Fos/Jun polypeptide partner is labelled with biotin by preparing a 200 µl solution of 220 µM (1 mg/ml) Fos/Jun in 20 mM TES pH 7.0. Thiol directed Biotin BMCC 8 µl (5 mg/ml) is added to this making the final concentration of Biotin 200 µM. The solution is mixed at room temperature for 2 hrs wrapped in tin foil. The biotinylated Fos/Jun peptide is mixed with purified Erk2-FJ resulting in Erk2 tagged with biotin.

Peptidic Binding Partners for Different Forms of ERK2.

Peptide 1 KCFLTEYVATRWYRAPEIMLC (181–197)

The above sequence is possibly a substrate for MEK1, so the threonine and tyrosine are replaced by alanine to give peptide 2:

KCFLAEAVATRWYRAPEIMLC

Peptide 1 and peptide 2 bind to the activated, phosphorylated form of ERK2. The peptide structure is stabilised by cyclisation through a disulphide bond between the two cysteines.

Alternatively, the unactivated conformation of ERK2 is detected by the binding peptides 3 and 4. Peptide 3 is derived from amino acids 169–186 of mouse ERK2:

CARVADPDHDHTGFLTEYVCK (169–186)

The above sequence is possibly a substrate for MEK1, so the threonine and tyrosine are replaced by alanine to give peptide 4:

CARVADPDHDHTGFLAEAVCK

Peptides 1 through 4 are labelled with fluorescein or rhodamine through amine directed labelling as described above.

Conditions for MEK1 Phosphorylation of ERK2

MEK1 phosphorylation of ERK2 is performed in 100 µl volume, 0 to 10 µg of purified ERK2-FJ labelled with fluorescein, 20 mM Hepes pH 7.3, 10 mM MgCl$_2$, 1 mM benzamidine, 1 mM dithiothreitol, and 1 mM ATP. The reaction is started by the addition of MEK1 (0–5 units), incubation is at 30° C. for 5 to 180 minutes. Detection of the activation state of ERK2 and thus measurement of MEK1 activity is monitored by the addition of specific binding partners to the phosphorylation reaction as described below. Detection of inhibitors of MEK1 activity is accomplished by adding the inhibitor to the reaction mixture prior to addition of MEK1.

FRET Solution Phase Assay of MEK1 Activity.

Fluorescein labelled ERK2-FJ is phosphorylated by MEK1 in the presence of peptide 1 or 2 labelled with rhodamine. Phosphorylated ERK2-FJ binds peptide 1 or 2 and results in FRET between the fluorescein and rhodamine. Thus the conformational change of ERK-FJ structure due to MEK1 phosphorylation is measured by the decrease in emission at 520 nm from fluorescein when excited at 490 nm.

Alternatively, Fluorescein labelled Erk2-FJ is phosphorylated by MEK1 in the presence of peptides 3 or 4 labelled with rhodamine. Unphosphorylated Erk2-FJ binds peptides 3 or 4 and results in FRET between the fluorescein and rhodamine, this will be disrupted due to phosphorylation. Thus the conformational change of ERK2-FJ structure due to MEK1 phosphorylation is measured by the increase in emission at 520 nm from fluorescein when excited at 490 nm, as the FRET interaction is abolished.

Inhibitors of MEK1 are detected by reversal of the fluorescent signal changes described above.

FP Assay of MEK 1 Activity

Unactivated ERK2 from Upstate Biotechnology is phosphorylated by MEK1 in the presence of peptide 1 or 2 labelled with fluorescein. Peptides 1 and 2 free in solution have a low polarisation value when excited with polarised light, 490 nm. Phosphorylated Erk2 binds peptide 1 or 2 and results in an increase in the polarisation value of the fluorescein. Thus the conformational change of Erk2 structure due to MEK1 phosphorylation is measured by the increase in fluorescein fluorescence polarisation at 520 nm when excited at 490 nm. Alternatively, unactivated Erk2 from Upstate Biotechnology is phosphorylated by MEK1 in the presence of peptide 3 or 4 labelled with fluorescein. Peptides 3 and 4 free in solution have a low polarisation value when excited with polarised light, 490 nm. Unphosphorylated Erk2 binds peptide 3 or 4 and results in an increase in the polarisation value of the fluorescein. Thus the conformational change of Erk2 structure due to MEK1 phosphorylation is measured by the decrease in fluorescein fluorescence polarisation at 520 nm when excited at 490 nm, due to release of peptide 3 or 4 from the Erk2.

Inhibitors of MEK1 are detected by reversal of the fluorescent signal changes described above.

Immobilised Assay of MEK1 Activity

MEK1 activity is measured by immobilising the Erk2 protein either through a hexaHis tag using Nickel/NTA derivatised microtitre plates, or by labelling the coiled-coil peptide of Erk2-FJ with biotin in place of fluorescein as described above. Erk2-biotin is bound to a black Reacti-Bind, Neutravidin plate (Pierce) and excess Erk2 washed away. The immobilised Erk2 is phosphorylated by MEK1 in the reaction conditions described above, then washed with buffer. The phosphorylation state is detected by addition of peptides as follows:

Addition of peptide 1 or 2 labelled with fluorescein to phosphorylated ERK2 results in binding of the peptides and an increase in fluorescence at 520 nm using 490 nm excitation. This signal is decreased in the presence of an inhibitor of MEK1. Addition of peptides 3 or 4 labelled with fluorescein will result in no fluorescent signal unless an inhibitor of MEK1 is also present, in which case the fluorescence at 520 nm will increase as peptide 3 and 4 bind to the unphosphorylated Erk2.

What is claimed is:

1. A method for determining the conformational state of a protein, comprising the steps of:
    a) contacting a protein with a labeled first binding partner which binds to said protein in a manner dependent on the conformational state of said protein and which generates a signal in a manner dependent on the binding of the first binding partner to the protein, and a labeled second binding partner which binds to said protein in a manner independent of the conformational state of said protein and which generates a signal in a manner dependent on the binding of the first binding partner to the protein, wherein said protein and said labeled first and second binding partner are not covalently bound; and
    b) detecting said protein by the binding of at least one of said labeled first binding partner and said labeled second binding partner to said protein wherein detection of a signal generated by said labeled first binding partner and/or said labeled second binding partner is an indicator of the conformational state of said protein.

2. A method for measuring the post-translational modifying activity of an enzyme, wherein the conformation of a protein is dependent upon the post-translational modification activity of the enzyme, the method comprising the steps of:
    a) contacting a protein comprising a site for post-translational modification with the enzyme;
    b) providing a labeled first binding partner which binds non-covalently to the protein in a manner dependent on the post-translational modification of the protein by the enzyme and which generates a signal in a manner dependent on said post-translational modification, and a second labeled binding partner which binds non-covalently to said protein and which generates a signal in a manner dependent on said post-translational modification;
    c) contacting the protein with the labeled first binding partner and the labeled second binding partner and detecting said protein by the binding to said protein of at least one of said labeled first binding partner and said labeled second binding partner, wherein detection of a signal generated by said labeled first binding partner and/or said labeled second binding partner indicates the post-translational modifying activity of the enzyme.

3. The method of claim 1 or 2, wherein the protein is immobilized on a solid phase substrate.

4. The method of claim 1 or 2, wherein the second binding partner is a capture ligand, and said protein that binds to said capture ligand is isolated from a protein that does not bind to said capture ligand.

5. The method of claim 4, wherein said capture ligand is bound to a solid phase substrate.

6. The method of claim 1 or claim 2, wherein at least one of said first or second binding partner is labeled with a label selected from the group consisting of a fluorescent label, a chemiluminescent label, a domain of an enzyme, a radiolabel, a chemical or enzymatic label and a heavy metal label.

7. The method of claim 1 or claim 2, wherein said first binding partner is labeled with a label detectable in a manner dependent on the binding of said first binding partner to the protein.

8. The method of claim 1 or claim 2, wherein both said first and second binding partners are fluorescently labeled, and the binding of said binding partners to the protein is assayed by fluorescence resonance energy transfer (FRET).

9. The method of claim 7, wherein both said first and second binding partners are labeled, with enzyme domains, which associate to form a functional receptor molecule when both binding partners are bound to the protein.

10. The method of claim 3, wherein said protein is covalently linked to the solid phase substrate.

11. The method of claim 1 or 2, further comprising the additional step of, after step (a), removing unbound labeled first binding partner to allow detection of the binding of the labeled first binding partner to the protein.

12. The method of claim 7, wherein the labeling of the protein by the binding of said first binding partner is detected by fluorescence correlation spectroscopy (FCS).

\* \* \* \* \*